United States Patent
Iwamoto et al.

(10) Patent No.: US 7,515,685 B2
(45) Date of Patent: Apr. 7, 2009

(54) FLUORESCENT X-RAY ANALYSIS METHOD AND DEVICE

(75) Inventors: Hiroshi Iwamoto, Osaka (JP); Yoshiyuki Tani, Osaka (JP); Takao Hisazumi, Osaka (JP); Yukihiro Iwata, Osaka (JP); Etsuyoshi Sakaguchi, Osaka (JP)

(73) Assignee: Panasonic Corporation, Osaka (JP)

( * ) Notice: Subject to any disclaimer, the term of this patent is extended or adjusted under 35 U.S.C. 154(b) by 279 days.

(21) Appl. No.: 11/587,930

(22) PCT Filed: Apr. 25, 2005

(86) PCT No.: PCT/JP2005/007774

§ 371 (c)(1),
(2), (4) Date: Oct. 26, 2006

(87) PCT Pub. No.: WO2005/106439

PCT Pub. Date: Nov. 10, 2005

(65) Prior Publication Data

US 2008/0192888 A1 Aug. 14, 2008

(30) Foreign Application Priority Data

Apr. 28, 2004 (JP) .............................. 2004-133134

(51) Int. Cl.
G01N 23/223 (2006.01)
(52) U.S. Cl. .......................................... 378/44; 378/79
(58) Field of Classification Search ................. 378/208, 378/44–50, 79, 117; 422/63–68.1, 82.5
See application file for complete search history.

(56) References Cited

U.S. PATENT DOCUMENTS

| 6,178,227 | B1 | 1/2001 | Sato |
| 6,359,962 | B1 | 3/2002 | Yagi |
| 2002/0015471 | A1 | 2/2002 | Yagi |

FOREIGN PATENT DOCUMENTS

| JP | 59-67409 A | 4/1984 |
| JP | 6-123716 A | 5/1994 |
| JP | 2000-162161 A | 6/2000 |
| JP | 2000-356607 A | 12/2000 |
| JP | 2003-156458 A | 5/2003 |
| JP | 2003156458 A * | 5/2003 |

OTHER PUBLICATIONS

Supplementary European Search Report issued in European Patent Application No. EP 05734381.6-1240/1744151 PCT/JP2005007774, dated Nov. 14, 2008.

* cited by examiner

*Primary Examiner*—Hoon Song
(74) *Attorney, Agent, or Firm*—McDermott Will & Emery LLP (57) ABSTRACT

In a fluorescent X-ray analysis method, a sample (1) is set on a sample stage (2) on an upper side of an X-ray irradiation chamber (7) and a sample cover (6) is closed from the upper part of the sample (1) to surround the sample (1), and then, a lower plane of the sample (1) is irradiated with X-ray for analysis. When the sample (1) is set on the sample stage (2) and the sample cover (6) is closed, a cover detecting means (8) detects that the sample cover (6) is closed and X-ray is automatically projected from an X-ray source (3) to start analysis.

2 Claims, 11 Drawing Sheets

1 sample
2 sample stage
3 X-ray source
4 X-ray detector
5 X-ray irradiation opening
6 sample cover
7 X-ray irradiation chamber
8 cover detection means
9 drive means

Fig. 1

1  sample
2  sample stage
3  X-ray source
4  X-ray detector
5  X-ray irradiation opening
6  sample cover
7  X-ray irradiation chamber
8  cover detection means
9  drive means

10  sample recognition means
11  processing means

12 sample recognition means

FLUORESCENT X-RAY ANALYSIS METHOD AND DEVICE

RELATED APPLICATIONS

This application is the U.S. National Phase under 35 U.S.C. § 371 of International Application No. PCT/JP2005/007774 filed on Apr. 25, 2005, which in turn claims the benefit of Japanese Application No. 2004-133134, filed on Apr. 28, 2004, the disclosures of which Applications are incorporated by reference herein.

TECHNICAL FIELD

The present invention relates to a fluorescent X-ray analysis device that detects secondary X-rays (known as fluorescent X-rays) generated secondarily from a sample when the sample is irradiated with X-rays, and analyzing the components contained in the sample.

BACKGROUND ART

A typical fluorescent X-ray analysis device is made up of an X-ray irradiation chamber equipped with at least an X-ray source and an X-ray detector, a sample stage on which a sample is placed and which has an X-ray irradiation opening above the X-ray irradiation chamber, and a sample cover which is a sealing and blocking type of structure for preventing X-rays from leaking outside and which is located on top of the sample stage (see Patent Document 1, for example).

The analysis method involves first placing a sample on the sample stage so as to close off the X-ray irradiation opening with the sample cover open. The sample cover is then lowered until it comes into contact with the sample stage so as to close off the sample and prevent X-rays from leaking outside. After this, an analysis start switch is turned on, X-rays are emitted from the X-ray source, and the lower side of the sample is irradiated through the X-ray irradiation opening. Fluorescent X-rays generated from this irradiation site are detected by the X-ray detector and converted into an electrical signal, and processing is performed to produce an X-ray spectrum expressed as energy versus intensity.

With the above-mentioned fluorescent X-ray analysis method and device, a sensor that detects when the sample cover is touching the sample stage is attached as a safety measure in order to prevent X-rays from leaking out to the surrounding area.

Patent Document 1: Japanese published unexamined patent application 2000-162161.

DISCLOSURE OF THE INVENTION

As mentioned above, conventional fluorescent X-ray analysis methods and devices included safety measures, but the work of opening and closing the sample cover that prevented X-ray leakage was separate from the work of emitting X-rays from the X-ray source and analyzing the sample, so a problem was that work efficiency was low in this analysis. Also, when the analysis start switch was turned on, X-rays were emitted from the X-ray source and analysis was commenced even if there was no sample on the sample stage or if the sample was not properly positioned, and this left open the possibility of incurring analysis work losses.

The present invention was conceived in an effort to solve the above problems, and it is an object thereof to provide a fluorescent X-ray analysis method and device with which analysis can be carried out more efficiently.

The present invention that achieves the stated object is constituted as follows.

The fluorescent X-ray analysis method of the present invention is a fluorescent X-ray analysis method in which a sample covered by a sample cover openably and closeably attached to a sample stage is irradiated with X-rays, and the fluorescent X-rays emitted from the sample are detected, comprising determining whether the sample cover is open or closed, and when the sample cover is closed, starting the X-ray irradiation of the sample. With this fluorescent X-ray analysis method, when the sample cover is closed, it is detected that the sample cover is closed and the X-ray irradiation of the sample begins automatically, so the sample can be analyzed more efficiently.

The fluorescent X-ray analysis device of the present invention comprises a sample stage upon which a sample can be placed, a sample cover openably and closeably attached to the sample stage, an X-ray irradiation unit for irradiating the sample with X-rays, a fluorescent X-ray detection unit for detecting fluorescent X-rays from the sample, a sample cover open/closed detection unit for detecting whether the sample cover is open or closed, and an X-ray irradiation starting unit for starting the X-ray irradiation of the sample when the sample cover is closed, on the basis of a signal from the sample cover open/closed detection unit. With this fluorescent X-ray analysis device, when the sample cover is closed, it is detected that the sample cover is closed and the X-ray irradiation of the sample begins automatically, so the sample can be analyzed more efficiently.

The fluorescent X-ray analysis method is a fluorescent X-ray analysis method in which a sample covered by a sample cover openably and closeably attached to a sample stage is irradiated with X-rays, and the fluorescent X-rays emitted from the sample are detected, comprising of determining whether the sample cover is open or closed, determining whether or not the sample has been placed on the sample stage, when the sample cover is closed, starting the X-ray irradiation of the sample, and even when the sample cover is closed, not irradiating the sample with X-rays if the sample has not been placed on the sample stage. With this fluorescent X-ray analysis method, since the X-ray irradiation of the sample is begun automatically when the sample cover is closed, the sample can be analyzed more efficiently. Also, since even when the sample cover is closed, the sample is not irradiated with X-rays if the sample has not been placed on the sample stage, no analysis work losses are incurred.

The fluorescent X-ray analysis device of the present invention comprises a sample stage upon which a sample can be placed, a sample cover openably and closeably attached to the sample stage, an X-ray irradiation unit for irradiating the sample with X-rays, a fluorescent X-ray detection unit for detecting fluorescent X-rays from the sample, a sample cover open/closed detection unit for detecting whether the sample cover is open or closed, a sample recognition unit for determining whether or not the sample has been placed on the sample stage, and an X-ray irradiation starting unit for starting the X-ray irradiation of the sample when the sample cover is closed, or, even when the sample cover is closed, not irradiating the sample with X-rays if the sample has not been put in place, on the basis of a signal from the sample cover open/closed detection unit and the sample recognition unit. With this fluorescent X-ray analysis device, since the X-ray irradiation of the sample is begun automatically when the sample cover is closed, the sample can be analyzed more efficiently. Also, since even when the sample cover is closed, the sample is not irradiated with X-rays if the sample has not been placed on the sample stage, no analysis work losses are incurred.

NUMERICAL REFERENCES 1 sample
2 sample stage
3 X-ray source (X-ray irradiation means)
4 X-ray detector (X-ray detection means)
5 X-ray irradiation opening
6 sample cover
7 X-ray irradiation chamber
8 cover detection means (cover open/closed detection means)
9 drive means (X-ray irradiation starting means)
10, 12 sample recognition means
11 processing means

DETAILED DESCRIPTION OF THE PREFERRED EMBODIMENT

With the fluorescent X-ray analysis method and device of the present invention, a sample placed on a sample stage at the top of an X-ray irradiation chamber, a sample cover is closed above the sample so as to enclosed the sample, and then the bottom side of the sample is irradiated with X-rays and analyzed, wherein this method is characterized in that when the sample is placed on the sample stage and the sample cover is closed, it is detected that the sample cover has been closed, and the emission of X-rays from an X-ray source and analysis are automatically commenced.

Also, this method is characterized in that when the sample cover is closed, it is detected that the sample cover has been closed, and the emission of X-rays from an X-ray source and analysis are automatically commenced only on the condition that it has been recognized that the sample is located above the X-ray irradiation opening in the sample stage.

First Embodiment

The fluorescent X-ray analysis method and device of the present invention will now be described through reference to FIGS. 1 to 8.

Figure 1:
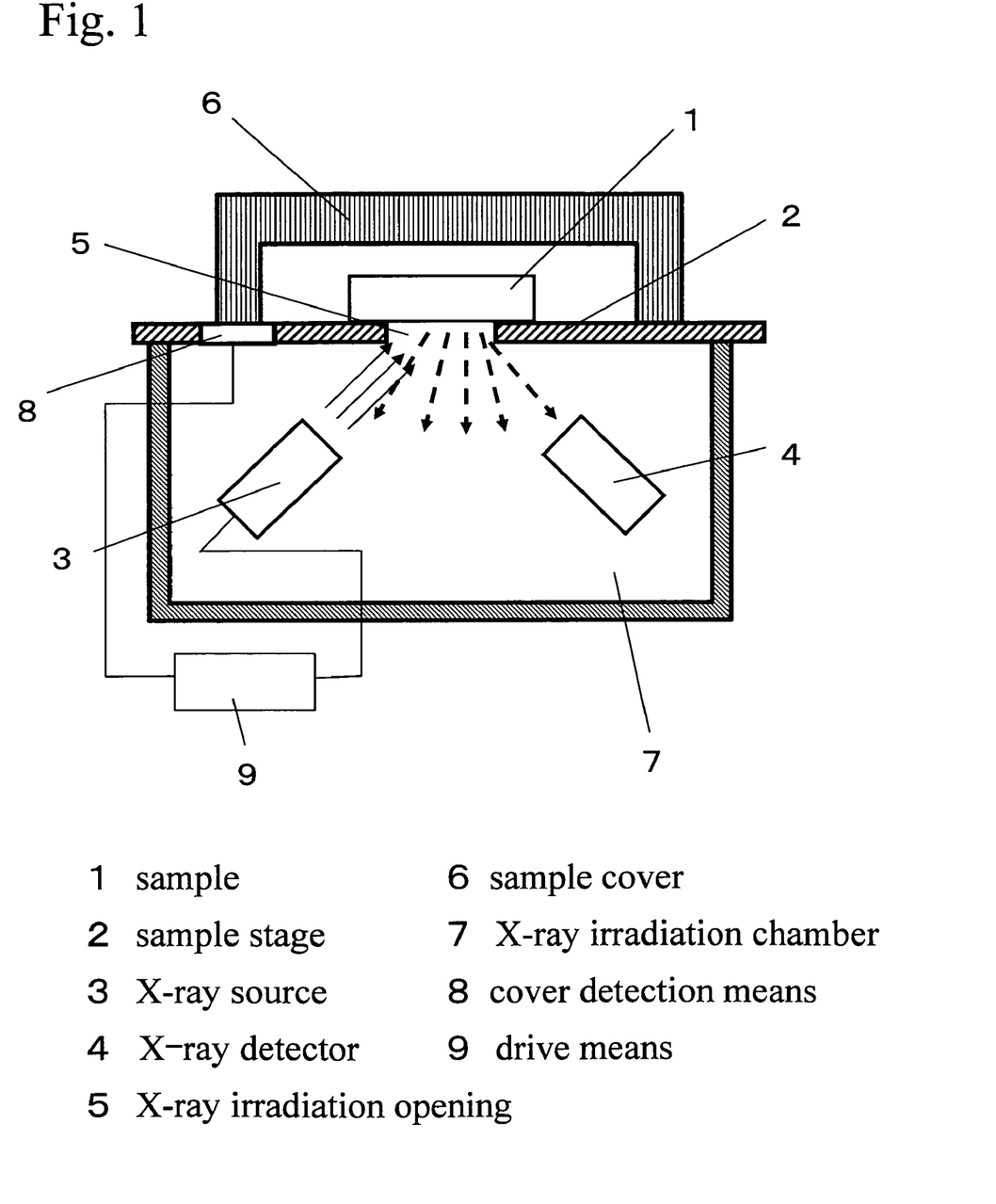
FIG. 1 is a simplified diagram of the fluorescent X-ray analysis device of the present invention.
Figure 2:
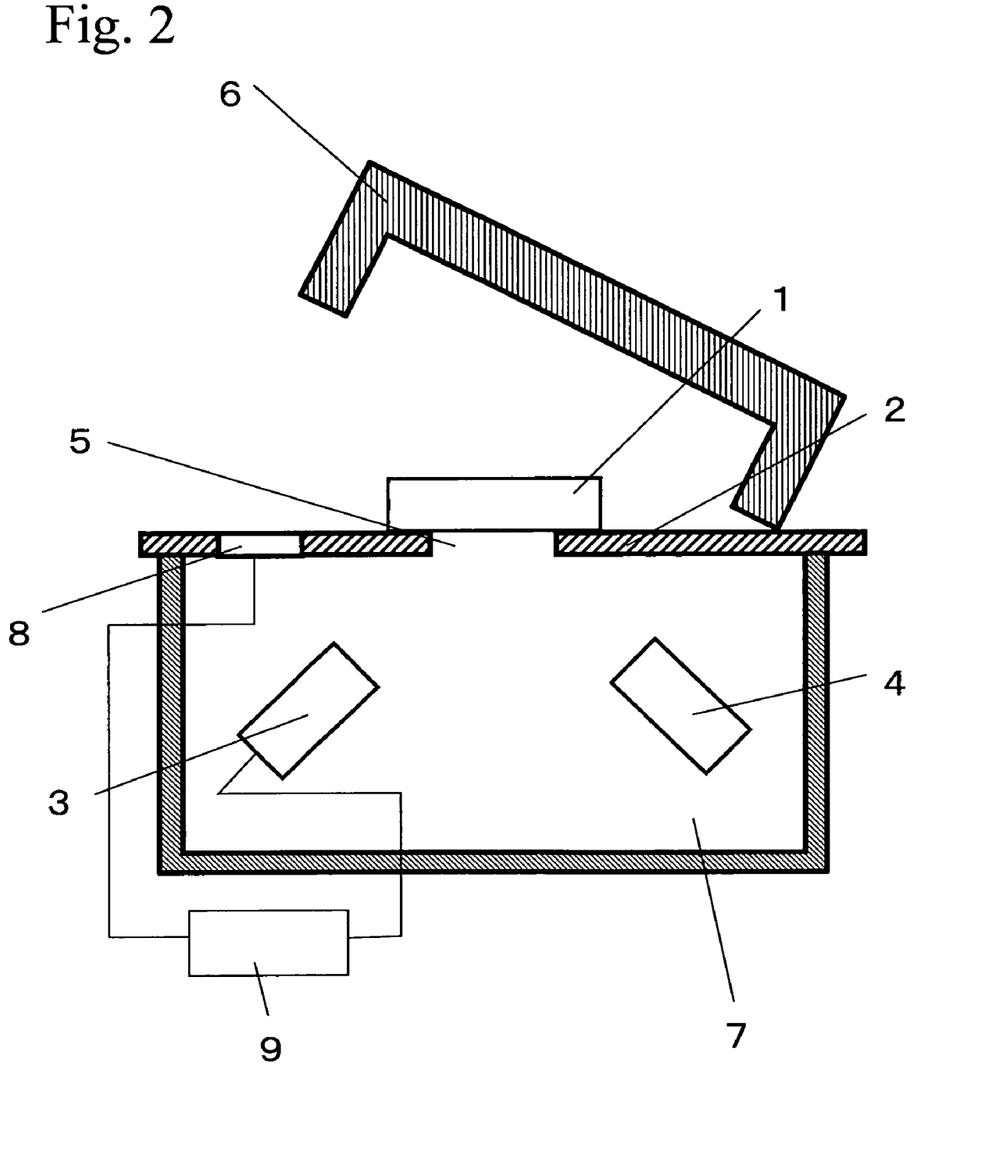
FIG. 2 is an operational diagram of the fluorescent X-ray analysis device of the present invention.
Figure 3:
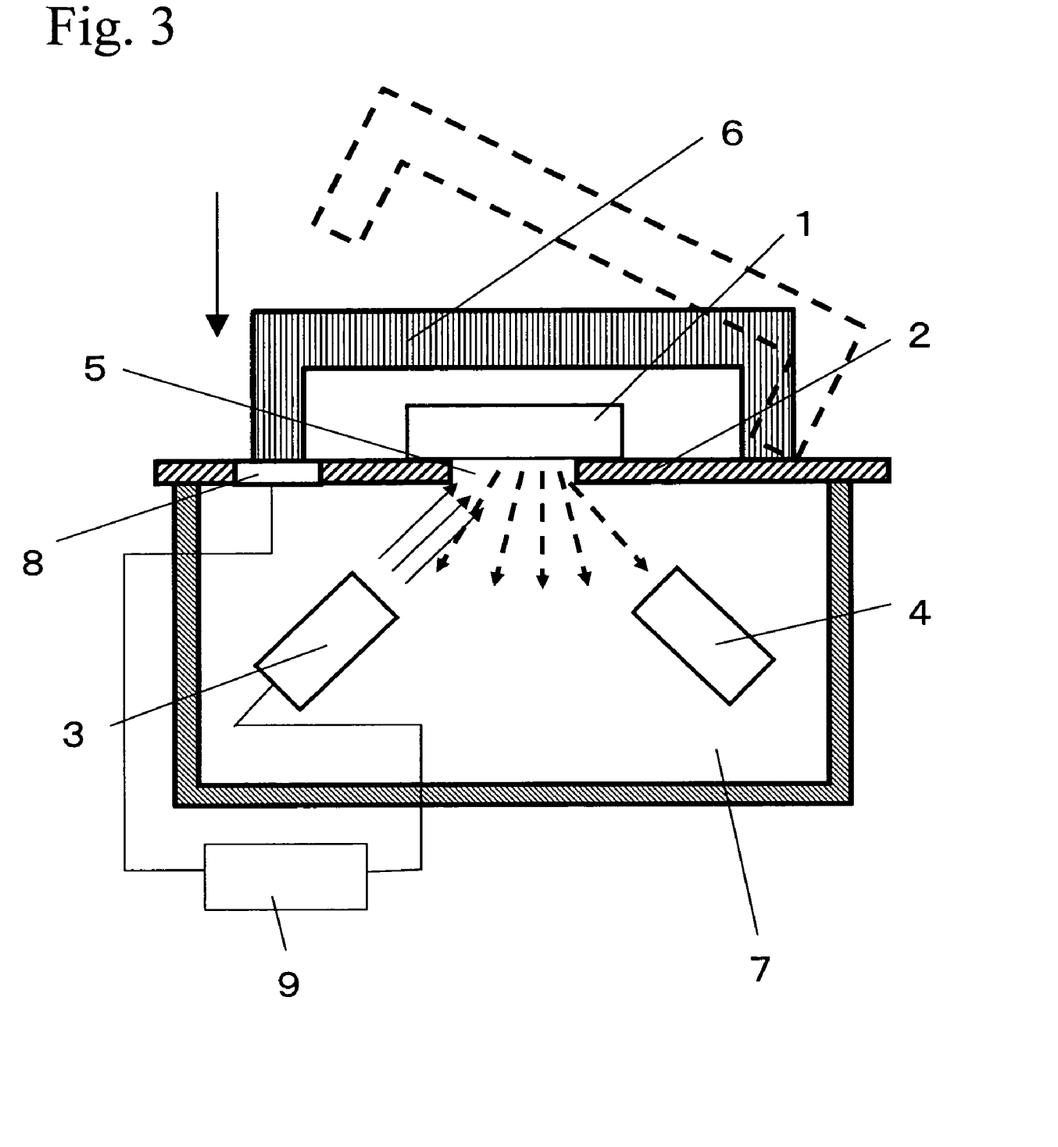
FIG. 3 is an operational diagram of the fluorescent X-ray analysis device of the present invention.
Figure 4:
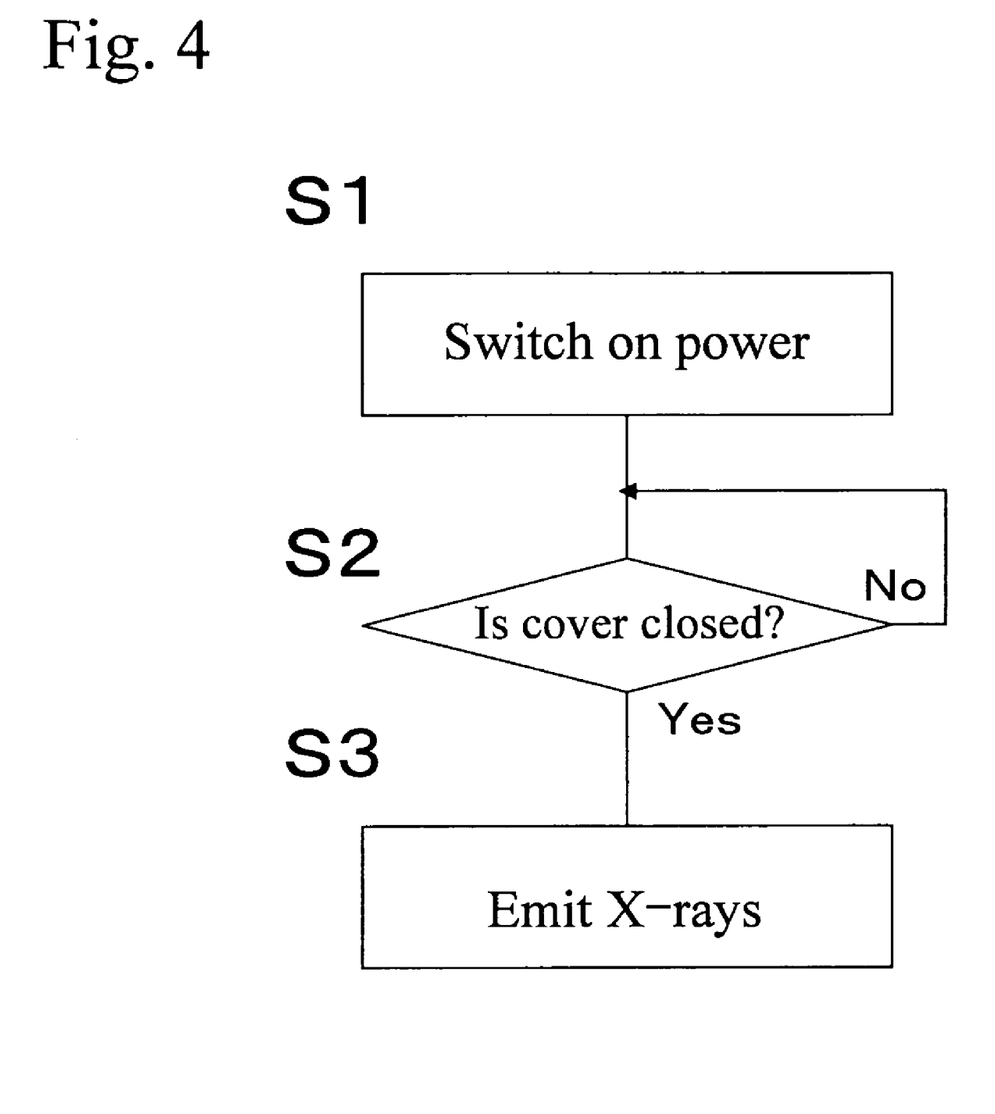
FIG. 4 is a flowchart of the fluorescent X-ray analysis device of the present invention.

FIG. 1 is a simplified diagram of the fluorescent X-ray analysis device of the present invention, FIGS. 2 and 3 are operational diagrams of the fluorescent X-ray analysis device of the present invention, and FIG. 4 is a flowchart of the fluorescent X-ray analysis device of the present invention. 1 is the sample to be measured, 2 is a sample stage on which the sample 1 is placed, 3 is an X-ray source, 4 is an X-ray detector, 5 is an X-ray irradiation opening, 6 is a sample cover, 7 is an X-ray irradiation chamber, 8 is a pressure sensor (cover detection means), and 9 is a drive means.

As shown in FIG. 1, the X-ray irradiation chamber 7 of the fluorescent X-ray analysis device is equipped with the X-ray source 3 and the X-ray detector 4 and is disposed on the lower side of the sample stage 2. The sample 1 is irradiated with X-rays from the X-ray source 3 through the X-ray irradiation opening 5 made in the sample stage 2, and fluorescent X-rays are detected by the X-ray detector 4. The sample cover 6, which can be opened and closed to prevent the leakage of X-rays, is attached at the top of the sample stage 2, and the pressure sensor 8 (cover detection means), which detects whether the sample cover 6 is open or closed, is attached to the sample stage 2. The drive means 9 performs X-ray irradiation from the X-ray source 3.

As shown in FIG. 2, the first step in the sample analysis is to place the sample 1 on the sample stage 2 with the sample cover 6 open. The sample cover 6 is then closed as shown in FIG. 3. At this point, the pressure sensor 8 (cover detection means) detects that the sample cover 6 has been closed, and upon receiving this signal the drive means 9 causes X-rays to be automatically emitted from the X-ray source 3, and the sample 1 to be irradiated through the X-ray irradiation opening 5 in the sample stage 2. Upon being irradiated with X-rays, the sample 1 generates fluorescent X-rays, which are detected by the X-ray detector 4 and then converted into an electrical signal, and processing is performed to produce an X-ray spectrum expressed as energy versus intensity. A laser sensor or the like may also be used for the cover detection means 8.

The fluorescent X-ray analysis method and device in this embodiment will now be described through reference to the flowchart in FIG. 4.

When power is switched on to the device (step S1), the drive means 9 determines on the basis of the signal from the cover detection means 8 whether or not the cover 6 is closed (whether or not there has been a transition from an open state to a closed state) (step S2). When the cover 6 is closed, the X-ray source 3 is driven so that the sample 1 is irradiated with X-rays (step S3). In other words, X-ray irradiation begins automatically as soon as the operator places the sample 1 on the sample stage 2 and then closes the sample cover 6.

The result of the above constitution and operation is that with the fluorescent X-ray analysis method and device of the present invention, when the sample cover is closed, it is detected that the sample cover has been closed and X-ray irradiation from the X-ray source and analysis are begun automatically, so the sample can be analyzed more efficiently.

Second Embodiment

Figure 5:
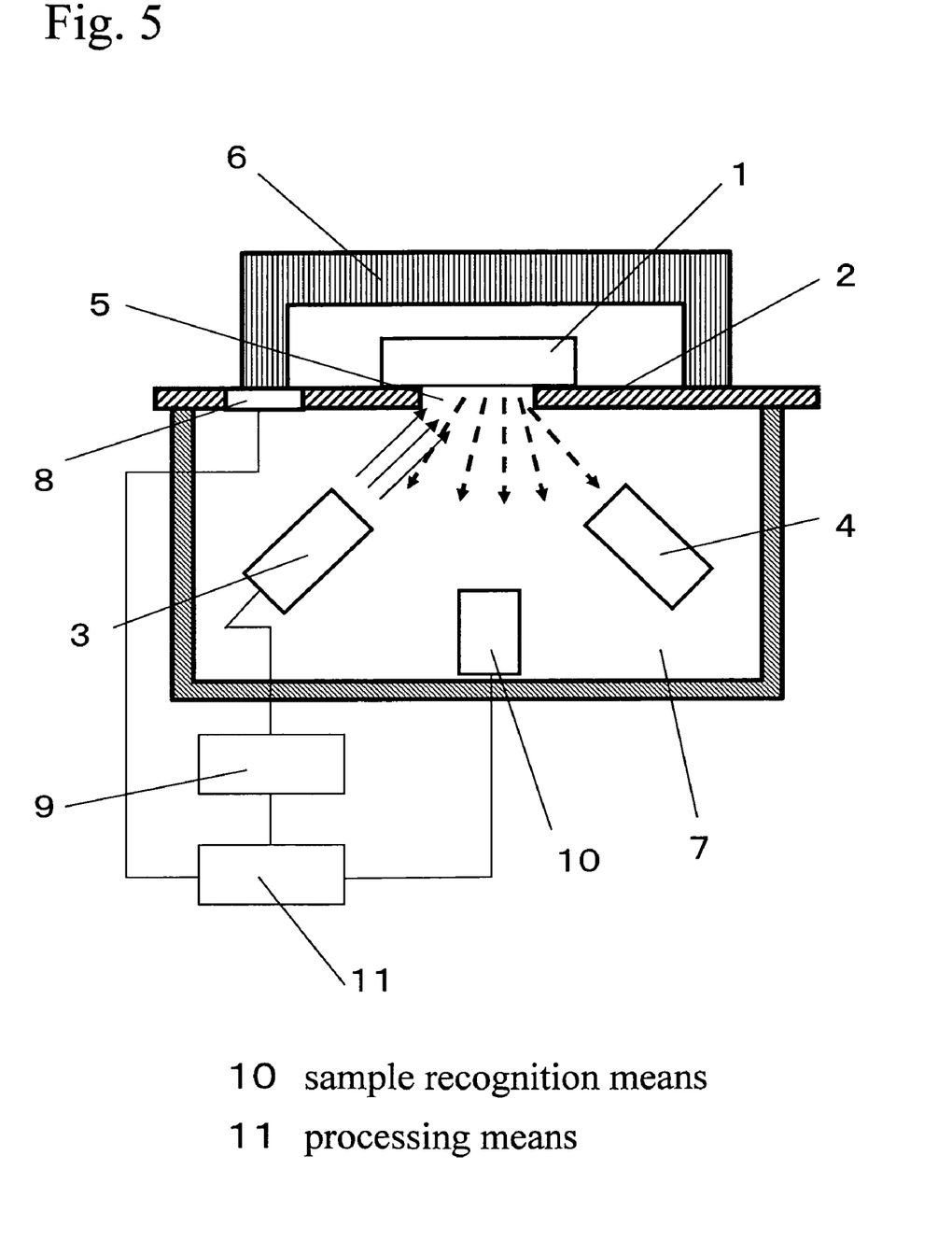
FIG. 5 is a simplified diagram of the fluorescent X-ray analysis device of the present invention.
Figure 6:
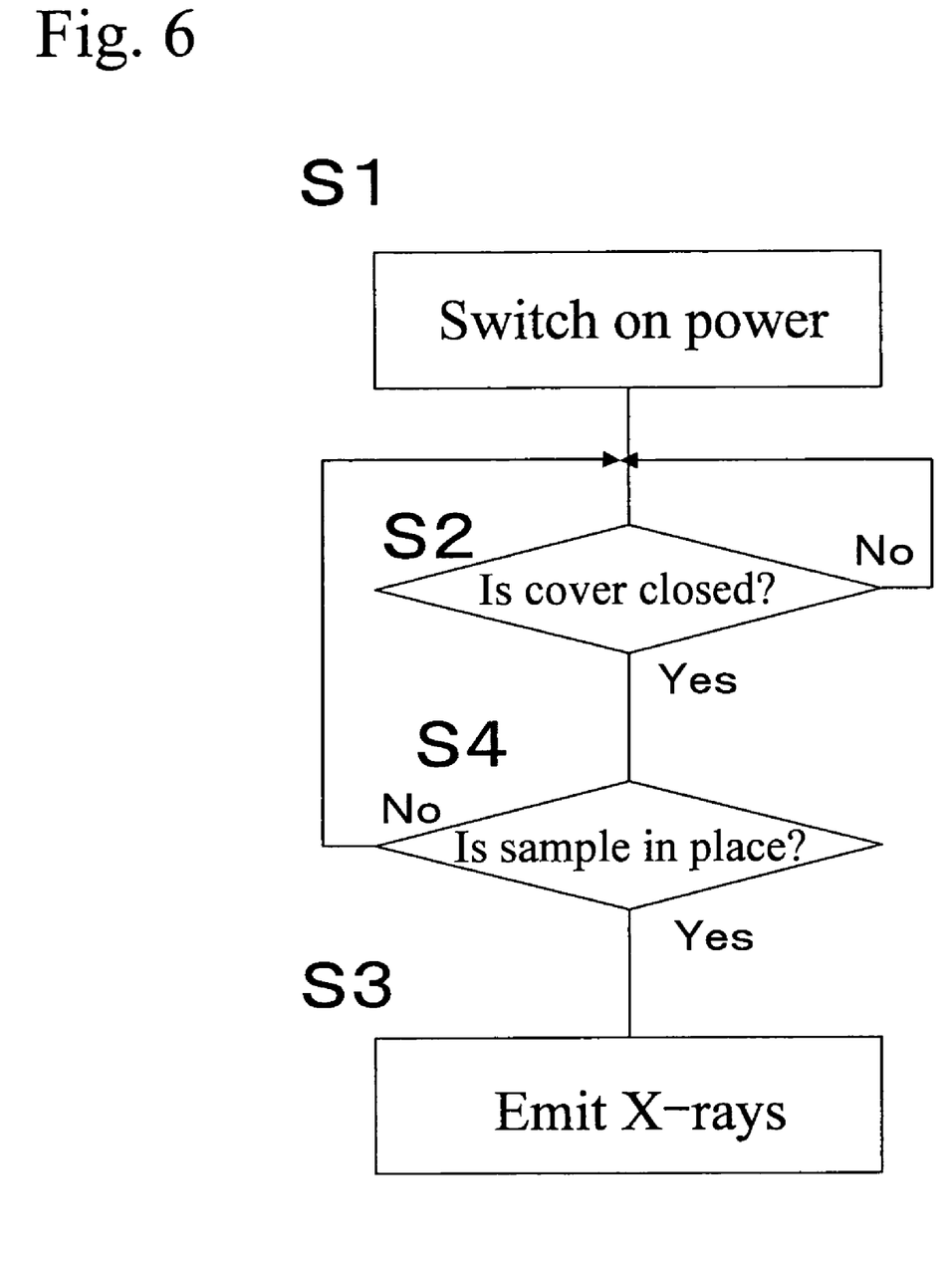
FIG. 6 is a flowchart of the fluorescent X-ray analysis device of the present invention.

FIG. 5 is a simplified diagram of the fluorescent X-ray analysis device of the present invention, and FIG. 6 is a flowchart of the fluorescent X-ray analysis device of the present invention. 10 is a CCD camera (sample recognition means), and 11 is a processing means.

As shown in FIG. 5, the fluorescent X-ray analysis device has a pressure sensor 8 (cover detection means) for detecting whether the sample cover 6 is open or closed, and the CCD camera 10 (sample recognition means) for recognizing whether the sample 1 is on the sample stage 2 in the X-ray irradiation chamber 7 and where the sample 1 is located thereon. A signal is sent to the drive means 9 by the processing means 11, which processes the signals from the cover detection means 8 and the sample recognition means 10, and X-rays are emitted from the X-ray source 3.

The first step in the sample analysis is to place the sample 1 on the sample stage 2 with the sample cover 6 open. The sample cover 6 is then closed. At this point, the pressure sensor 8 (cover detection means) detects that the sample cover 6 has been closed, and the CCD camera 10 (sample recognition means) recognizes whether the sample 1 is on the sample stage 2 and where the sample 1 is located thereon. A signal indicating that the sample cover 6 has been closed, and a signal indicating that it has been recognized that the sample 1 is positioned over the X-ray irradiation opening 5 in the sample stage 2 are sent to the processing means 11.

When the processing means 11 receives these two signals, the drive means 9 automatically causes X-rays to be emitted from the X-ray source 3, and the sample 1 to be irradiated through the X-ray irradiation opening 5 in the sample stage 2. Upon being irradiated with X-rays, the sample 1 generates fluorescent X-rays, which are detected by the X-ray detector 4 and then converted into an electrical signal, and processing is performed to produce an X-ray spectrum expressed as energy versus intensity.

The fluorescent X-ray analysis method and device in this embodiment will now be described through reference to the flowchart in FIG. 6.

When power is switched on to the device (step S1), the processing means 11 determines on the basis of the signal from the cover detection means 8 whether or not the cover 6 is closed (whether or not there has been a transition from an open state to a closed state) (step S2). When the cover 6 is closed, the processing means 11 determines on the basis of the signal from the sample recognition means 10 whether or not the sample 1 is in place on the stage (step S4). If the sample 1 is in place on the stage, the processing means 11 directs the drive means 9 to cause X-rays to be emitted from the X-ray source 3. The X-ray source 3 is driven so that the sample 1 is irradiated with X-rays (step S3). In other words, X-ray irradiation begins automatically as soon as the operator places the sample 1 on the sample stage 2 and then closes the sample cover 6. If the sample 1 has not been put in place, however, X-ray irradiation is not performed.

The result of the above constitution and operation is that with the fluorescent X-ray analysis method and device of the present invention, when the sample cover is closed, it is detected that the sample cover has been closed, and it is recognized that the sample is in place above the X-ray irradiation opening in the sample stage, and only when these two conditions are met are X-rays automatically emitted from the X-ray source and analysis performed, so the sample can be analyzed more efficiently, and no analysis work losses are incurred.

Also, since the sample is recognized with a CCD camera, it can be viewed from a distance that will not affect the fluorescent X-ray analysis. Furthermore, the image produced by the CCD camera can be checked visually, making it possible to check that the sample is in the proper location on the sample stage.

A photointerrupter consisting of an LED and a phototransistor may be used, for example, instead of a CCD camera as the sample recognition means. In this case, one of the members constituting the photointerrupter is fixed to the sample cover. A reflective photosensor may also be used.

Third Embodiment

Figure 7:
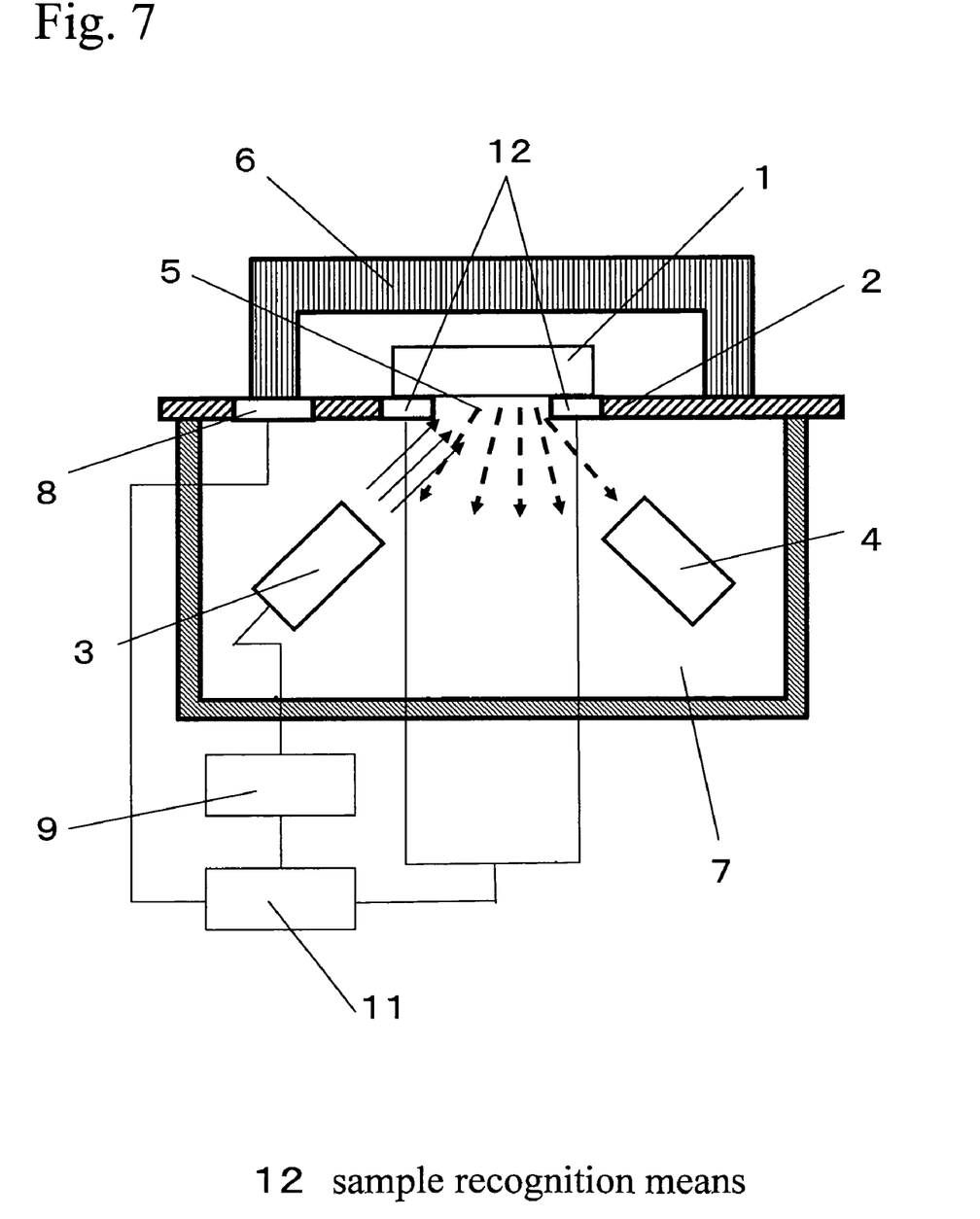
FIG. 7 is a simplified diagram of the fluorescent X-ray analysis device of the present invention.
Figure 8:
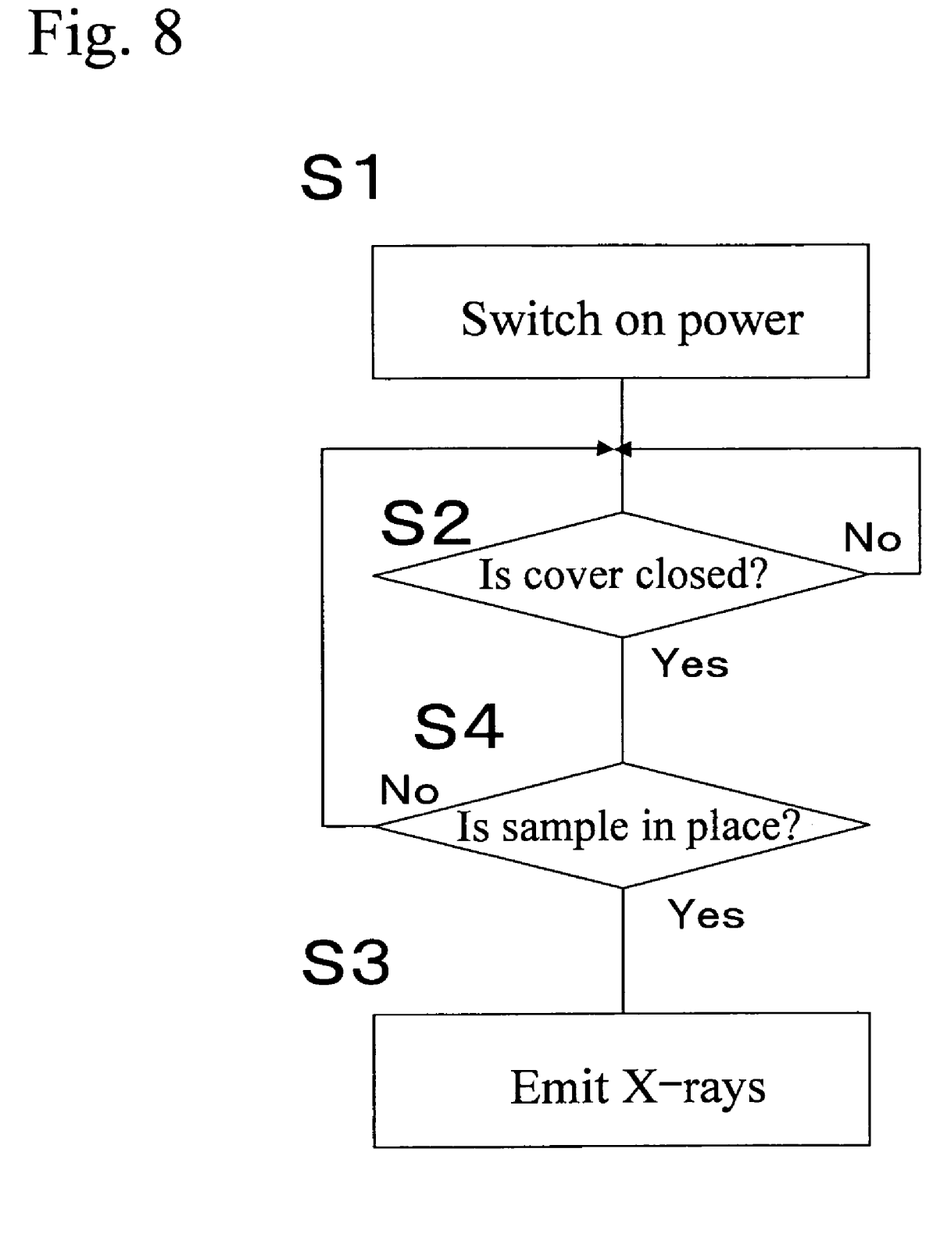
FIG. 8 is a flowchart of the fluorescent X-ray analysis device of the present invention.

FIG. 7 is a simplified diagram of the fluorescent X-ray analysis device of the present invention, and FIG. 8 is a flowchart of the fluorescent X-ray analysis device of the present invention. 12 is a pressure sensitive device (sample recognition means).

As shown in FIG. 7, the fluorescent X-ray analysis device is such that the pressure sensor 8 (cover detection means) that detects whether the sample cover 6 is open or closed, and the pressure sensitive device 12 (sample recognition means) that recognizes whether the sample 1 is on the sample stage 2 and the location of the sample 1 thereon, are incorporated in the sample stage 2. A signal is sent to the drive means 9 by the processing means 11, which processes the signals from the cover detection means 8 and the sample recognition means 12, and X-rays are emitted from the X-ray source 3.

The first step in the sample analysis is to place the sample 1 on the sample stage 2 with the sample cover 6 open. The sample cover 6 is then closed. At this point, the pressure sensor 8 (cover detection means) detects that the sample cover 6 has been closed, and the pressure sensitive device 12 (sample recognition means) checks whether the sample 1 is on the sample stage 2 and the location of the sample 1 thereon. A signal indicating that the sample cover 6 has been closed, and a signal indicating that it has been recognized that the sample 1 is positioned over the X-ray irradiation opening 5 in the sample stage 2 are sent to the processing means 11.

When the processing means 11 receives these two signals, the drive means 9 automatically causes X-rays to be emitted from the X-ray source 3, and the sample 1 to be irradiated through the X-ray irradiation opening 5 in the sample stage 2. Upon being irradiated with X-rays, the sample 1 generates fluorescent X-rays, which are detected by the X-ray detector 4 and then converted into an electrical signal, and processing is performed to produce an X-ray spectrum expressed as energy versus intensity.

The fluorescent X-ray analysis method and device in this embodiment will now be described through reference to the flowchart in FIG. 8.

When power is switched on to the device (step S1), the processing means 11 determines on the basis of the signal from the cover detection means 8 whether or not the cover 6 is closed (whether or not there has been a transition from an open state to a closed state) (step S2). When the cover 6 is closed, the processing means 11 determines on the basis of the signal from the sample recognition means 10 whether or not the sample 1 is in place on the stage (step S4). If the sample 1 is in place on the stage, the processing means 11 directs the drive means 9 to cause X-rays to be emitted from the X-ray source 3. The X-ray source 3 is driven so that the sample 1 is irradiated with X-rays (step S3). In other words, X-ray irradiation begins automatically as soon as the operator places the sample 1 on the sample stage 2 and then closes the sample cover 6. If the sample 1 has not been put in place, however, X-ray irradiation is not performed.

The result of the above constitution and operation is that with the fluorescent X-ray analysis method and device of the present invention, when the sample cover is closed, it is detected that the sample cover has been closed, and it is recognized that the sample is in place above the X-ray irradiation opening in the sample stage, and only when these two conditions are met are X-rays automatically emitted from the X-ray source and analysis performed, so the sample can be analyzed more efficiently, and no analysis work losses are incurred. Also, since the sample on the sample stage is recognized by a pressure sensitive device, the sample can be reliably recognized even in the dark.

Fourth Embodiment

In the above embodiments, the X-ray irradiation of the sample was started when the X-ray source was driven by a drive means, but the X-ray irradiation may instead be started by using a shutter driver to open a shutter.

Figure 9:
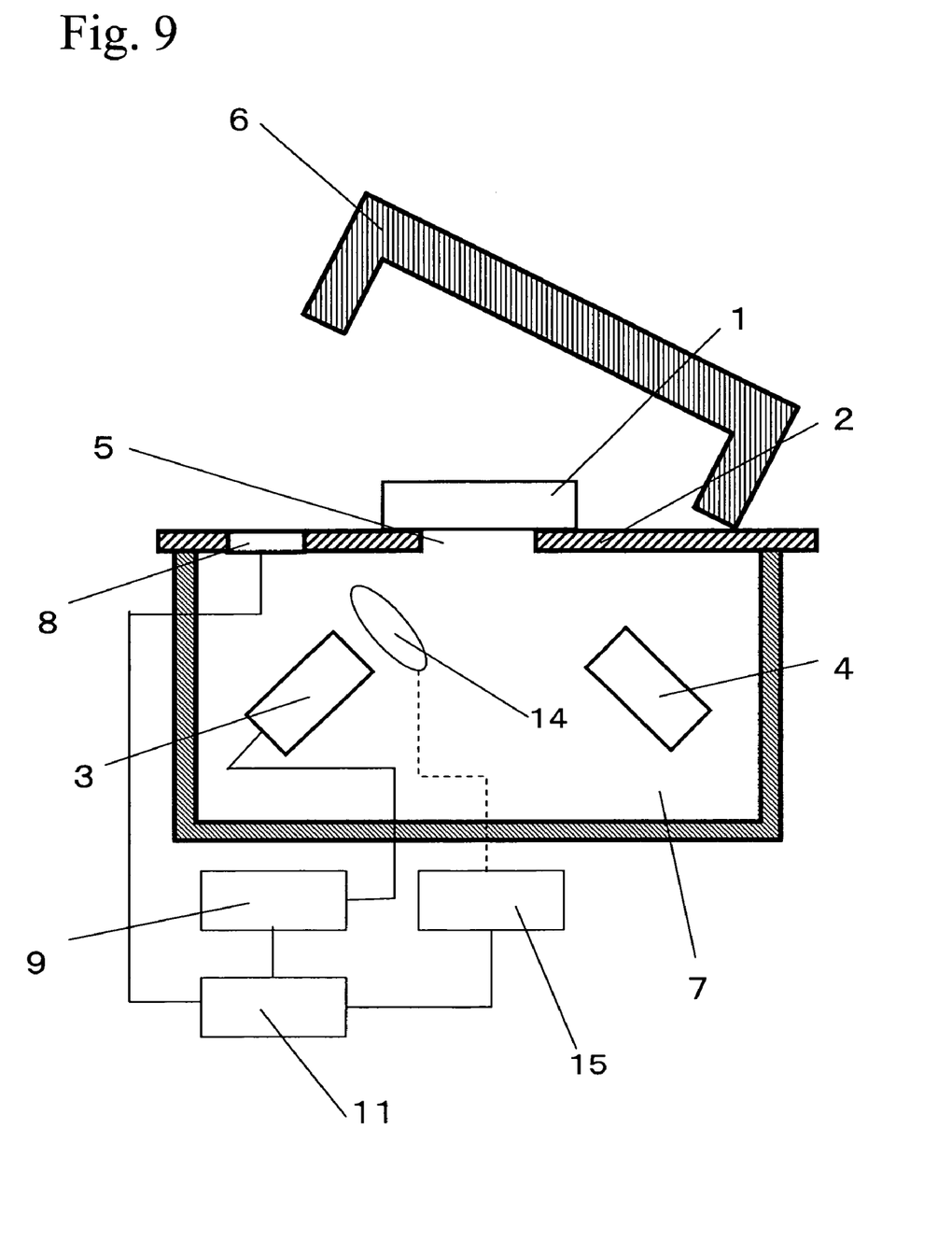
FIG. 9 is an operational diagram of the fluorescent X-ray analysis device of the present invention.
Figure 10:
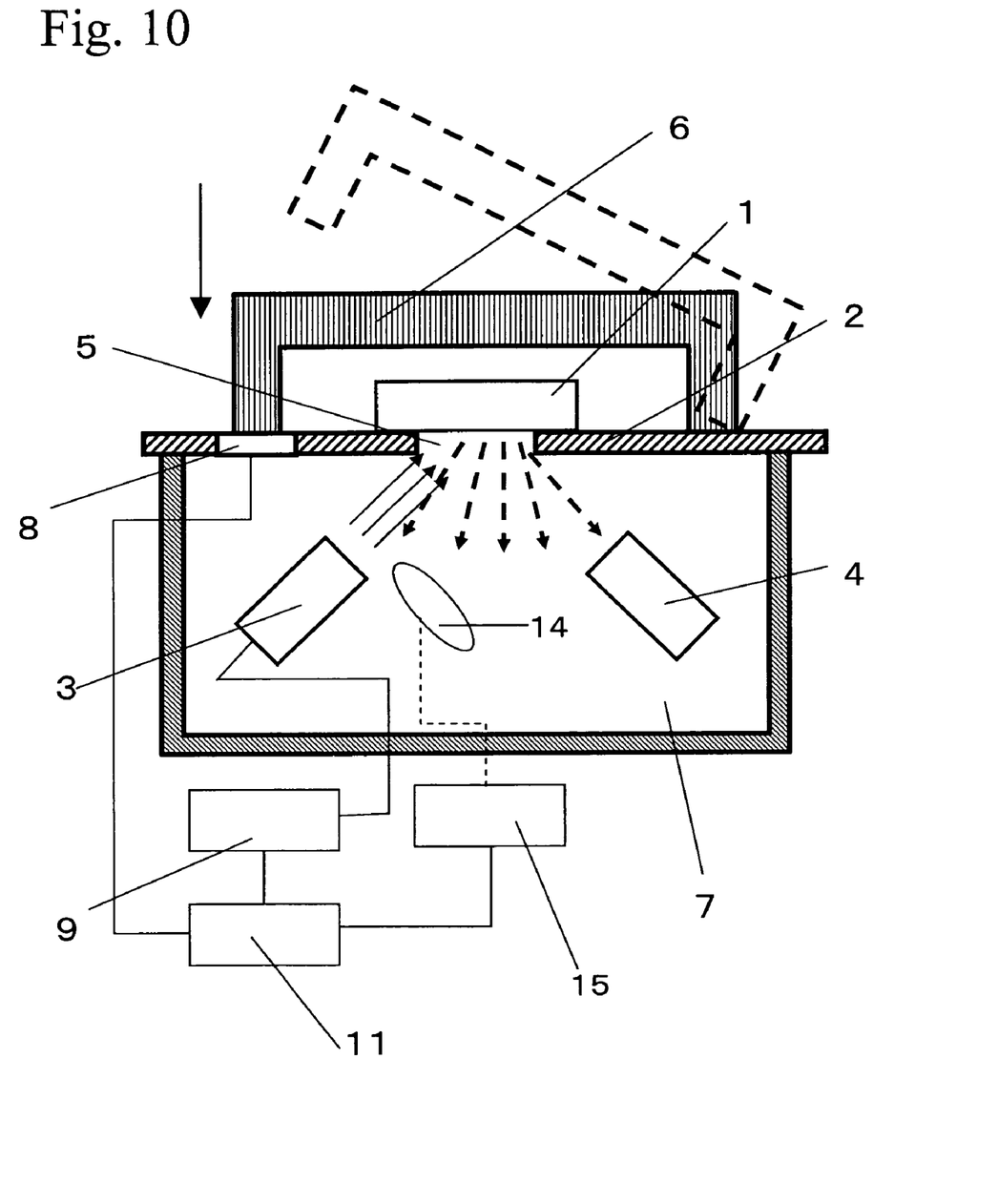
FIG. 10 is an operational diagram of the fluorescent X-ray analysis device of the present invention.

With the fluorescent X-ray analysis device shown in FIGS. 9 and 10, a shutter 14 is disposed between the X-ray source 3 and the sample 1. The shutter 14 may be made of a material and have a thickness that allow emitted X-rays to be safely blocked. An example is the use of tungsten or stainless steel as the material. The shutter 14 can be moved by a shutter driver 15 between a closed position that covers the X-ray source 3, and an open position that leaves the X-ray source 3 open.

Figure 11:
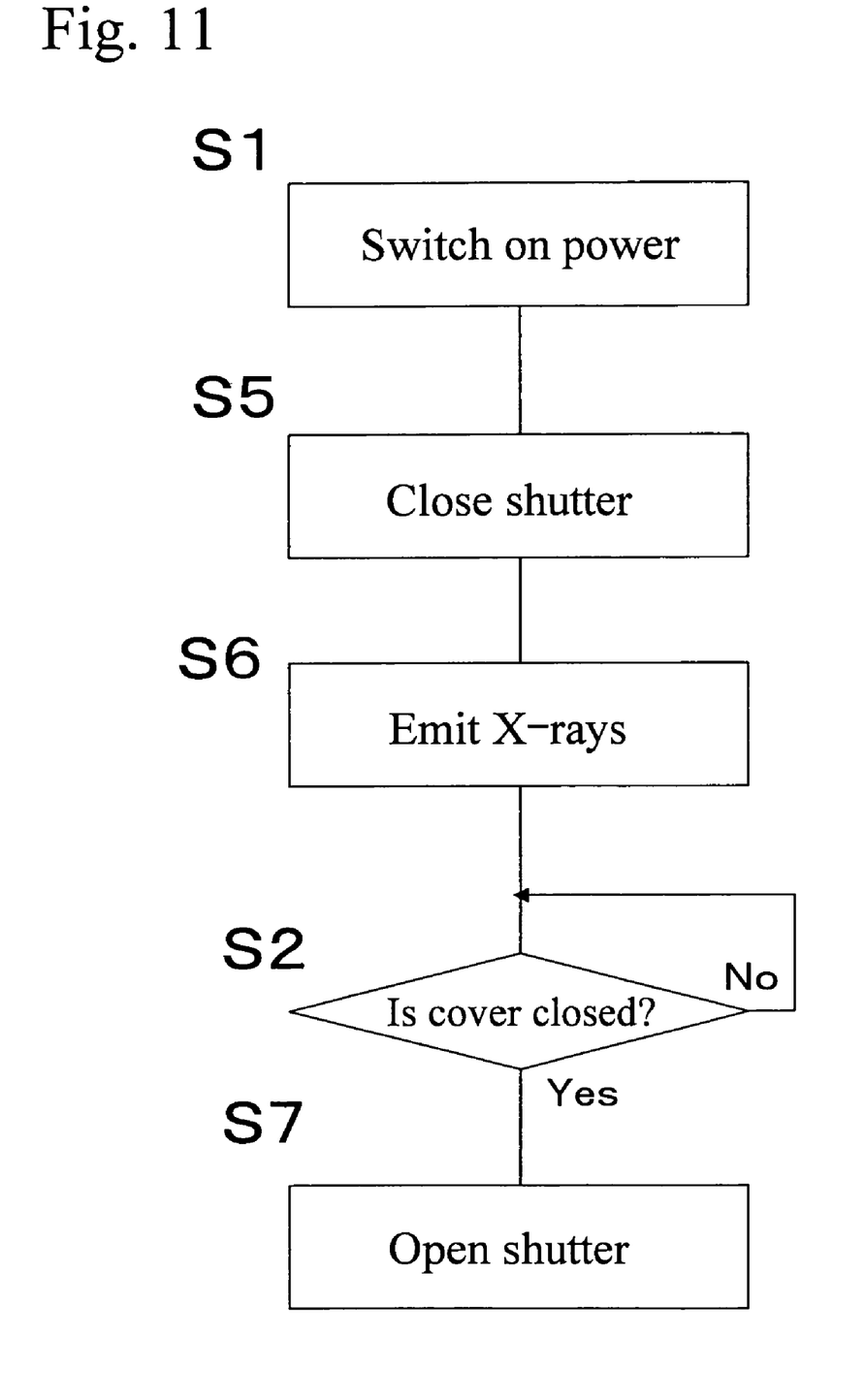
FIG. 11 is a flowchart of the fluorescent X-ray analysis device of the present invention.

The fluorescent X-ray analysis method and device in this embodiment will now be described through reference to the flowchart in FIG. 11.

When power is switched on to the device (step S1), the shutter driver 15 moves the shutter 14 to the closed position shown in FIG. 9, under direction by a signal from the processing means 11 (step S5). The drive means 9 then drives the X-ray source 3 under direction by a signal from the processing means 11, so that X-rays are emitted (step S6). In this state, the shutter 14 keeps the X-rays from reaching the sample 1, and leakage to the outside is kept to a minimum. The processing means 11 determines on the basis of the signal from the cover detection means 8 whether or not the cover 6 is closed (whether or not there has been a transition from an open state to a closed state) (step S2). When the cover 6 is closed, the processing means 11 sends a signal to the shutter driver 15, and the shutter 14 is moved to its open position (step S7). As a result, as shown in FIG. 10, the sample 1 is irradiated with X-rays from the X-ray source 3. In other words, X-ray irradiation begins automatically as soon as the operator places the sample 1 on the sample stage 2 and then closes the sample cover 6. If the sample 1 has not been put in place, however, X-ray irradiation is not performed.

The result of the above constitution and operation is that with the fluorescent X-ray analysis method and device of the present invention, when the sample cover is closed, this automatically starts the emission of X-rays from the X-ray source and analysis, so the sample can be analyzed more efficiently.

Embodiments of applying the present invention were described above, but the present invention is not limited to or by these embodiments, and various modifications and corrections are possible within the scope of the present invention.

INDUSTRIAL APPLICABILITY

In addition to its use in research and development applications, the fluorescent X-ray analysis method and device of the present invention can also be utilized in industrial settings with the aim of streamlining and speeding up measurement work.

The invention claimed is:

1. A fluorescent X-ray analysis method in which a sample covered by a sample cover openably and closeably attached to a sample stage is irradiated with X-rays, and the fluorescent X-rays emitted from the sample are detected, comprising:
   determining whether the sample cover is open or closed;
   determining whether or not the sample has been placed on the sample stage;
   when the sample cover is closed, starting the X-ray irradiation of the sample; and
   even when the sample cover is closed, not irradiating the sample with X-rays if the sample has not been placed on the sample stage.

2. A fluorescent X-ray analysis device, comprising:
   a sample stage upon which a sample can be placed;
   a sample cover openably and closeably attached to the sample stage;
   an X-ray irradiation unit for irradiating the sample with X-rays;
   a fluorescent X-ray detection unit for detecting fluorescent X-rays from the sample;
   a sample cover open/closed detection unit for detecting whether the sample cover is open or closed;
   a sample recognition unit for determining whether or not the sample has been placed on the sample stage; and
   an X-ray irradiation starting unit for starting the X-ray irradiation of the sample when the sample cover is closed, or, even when the sample cover is closed, not irradiating the sample with X-rays if the sample has not been put in place, on the basis of a signal from the sample cover open/closed detection unit and the sample recognition unit.

* * * * *